United States Patent [19]

Dusza et al.

[11] 4,376,122
[45] Mar. 8, 1983

[54] NOVEL 3-SUBSTITUTED AMINO-1-HETEROARYL-2-PYRAZOLINES

[75] Inventors: John P. Dusza, Nanuet, N.Y.; Joseph P. Joseph, Montvale, N.J.; Seymour Bernstein, New City, N.Y.

[73] Assignee: American Cyanamid Company, Stamford, Conn.

[21] Appl. No.: 282,826

[22] Filed: Jul. 13, 1981

[51] Int. Cl.$^3$ ................. C07D 417/02; A61K 31/428
[52] U.S. Cl. .................................... 424/270; 548/162
[58] Field of Search ........................ 548/162; 424/270

[56] References Cited

U.S. PATENT DOCUMENTS 4,054,574 10/1977 Wu ...................................... 548/162

Primary Examiner—Robert Gerstl
Attorney, Agent, or Firm—Anne M. Rosenblum

[57] ABSTRACT

This disclosure describes novel 3-substituted amino-1-heteroaryl-2-pyrazolines and their C5 analogs, effective an antibacterial and antifungal agents.

4 Claims, No Drawings

NOVEL 3-SUBSTITUTED AMINO-1-HETEROARYL-2-PYRAZOLINES

PRIOR ART

The compounds of the present invention have no known prior art.

Related references:

1. R. Battisti, et al., U.S. Pat. No. 4,149,005 (Apr. 10, 1979) describes compounds of the formula:

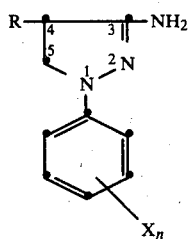

where R is H or $CH_3$, X is H, Br, Cl, alkyl, alkoxy or carboxyalkyl groups with from 1 to 4 carbon atoms or $CF_3$; and n is 1 or 2. Battisti used these compounds as intermediates in the preparation of 1-phenyl-3-aminopyrazoles as coupling components in azo dye manufacture. Related foreign patents are: Ger. Offen. No. 2,727,706; French Pat. No. 2,355,834; Gr. Br. Pat. No. 1,515,500; Belgium Pat. No. 855,944; Netherland Pat. No. 7,706,760 and Japan Pat. No. 28,168.

2. G. A. Higgs, et al.; (Wellcome Research Laboratories); Biochemical Pharmacology, 28 1959 (1979) describes 3-amino-1-[m-(trifluoromethyl)phenyl]-2-pyrazoline (BW 755C) of the formula:

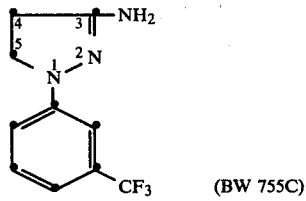

This compound is reported to have anti-inflammatory activity.

BRIEF SUMMARY OF THE INVENTION

This invention relates to new organic compounds and more particularly is concerned with novel C5 analogs of 3-substituted amino-1-heteroaryl-2-pyrazolines which may be represented by the following general formulae:

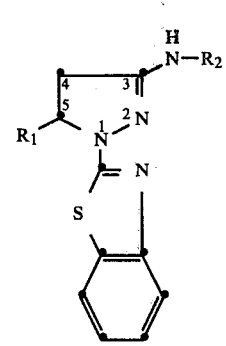

wherein $R_1$ may be phenyl and p-tolyl; $R_2$ is $CO-R_3$ where $R_3$ is lower alkyl ($C_1$-$C_4$) and the pharmacologically acceptable acid-addition salts thereof.

DETAILED DESCRIPTION OF THE INVENTION

The novel compounds of the present invention are generally obtainable as white to pale yellow crystalline solids having characteristic melting points and absorption spectra. The bases are appreciably soluble in solvents such as acetone, ethanol, toluene, methylene chloride and the like but are relatively insoluble in water. The organic bases of the present invention form non-toxic acid-addition salts with a variety of pharmacologically acceptable organic and inorganic salt forming reagents. Thus, acid-addition salts, formed by admixture of the organic free base with one or two equivalents of an acid, suitably in a neutral solvent, are formed with such acids as sulfuric, phosphoric, hydrochloric, hydriodic, sulfamic, citric, lactic, fumaric, succinic, tartaric, acetic, benzoic, gluconic, ascorbic, and the like. The acid-addition salts are relatively insoluble in non-polar organic solvents such as diethyl ether, benzene, toluene, and the like but are appreciably soluble in water. For purposes of this invention, the free bases are equivalent to their non-toxic acid-addition salts.

Preparation of the novel 3-substituted amino-1-heteroaryl-2-pyrazolines IV of the instant invention, which are active as antibacterial and/or antifungal agents is accomplished by the adaptation of the procedure of Duffin, G. F. and Kendall, J. D., J. Chem. Soc., 1954, 408; in accordance with the following reaction scheme:

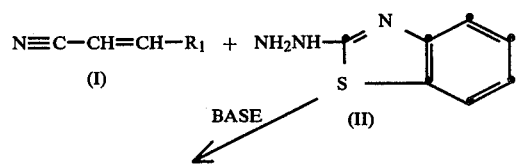

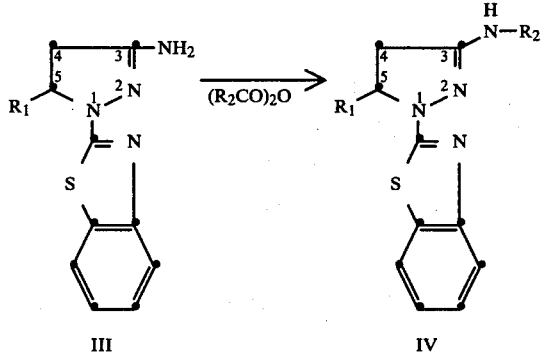

wherein $R_1$ and $R_2$ are as hereinabove defined.

In accordance with the above reaction scheme, 2-hydrazinobenzothiazole II is reacted with an α,β-unsaturated nitrile I, such as cinnamonitrile or 4-methylcinnamonitrile in a base catalyzed condensation procedure which is catalyzed with a base such as sodium ethoxide or choline hydrate in a suitable solvent, such as absolute ethanol. The reaction mixture is preferably refluxed for 4–16 hours, then, preferably, the solvent is reduced in volume, and the precipitate is collected by filtration and purified by standard procedures, e.g., it is washed with a solvent such as hexane or ethanol to yield the 3-amino-1-heteroaryl-2-pyrazoline compounds III.

The pyrazoline compound III is subjected to N-acylation by treating with an acylating agent such as acetic anhydride or propionic anhydride (with or without a catalyst such as 4-dimethylaminopyridine) at room temperature for 2–48 hours to yield the corresponding novel 3-substituted amino-1-heteroaryl-2-pyrazoline derivatives IV of the present invention which for the most part may be recrystallized from dichloromethane-hexane after passage through a hydrous magnesium silicate.

The compounds of the instant invention have utility as pharmacological agents. They are active as antibacterial and/or antifungal agents.

Representative compounds of the present invention have been proven active in vitro as antibacterial and/or antifungal agents when tested by such procedures as the standard agar dilution procedure.

Compounds proven active in this test are:
N-[1-(2-Benzothiazolyl)-5-p-tolyl-2-pyrazolin-3-yl]propionamide
N-[1-(2-Benzothiazolyl)-5-phenyl-2-pyrazolin-3-yl]acetamide.

The compounds of the present invention have been found to be highly useful as antibacterial and antifungal agents in mammals, when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the active ingredient for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active ingredient may be administered in any convenient manner such as by the oral, intravenous, intramuscular, intra-articular, topical or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, phenyl mercuric nitrate, benzalkonium chloride, phenethyl alcohol, p-chlorophenyl-α-glycerol ether, methyl and propyl parabens, and thimerosal. As a practical matter it is also convenient to employ antioxidants. Suitable antioxidants include, for example sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The compounds of this invention are equally adapted to intravenous administration when diluted with water or diluents employed in intravenous therapy such as isotonic glucose in appropriate quantities. For intravenous use, initial concentrations down to about 0.05 to 0.25 mg./ml. of active compound are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose, or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

This invention will be described in greater detail in conjunction with the following examples.

EXAMPLE 1

N-[1-(2-Benzothiazolyl)-5-p-tolyl-2-pyrazolin-3-yl]propionamide (A) A 500 mg. amount of sodium metal is dissolved in 250 ml. of absolute ethanol, then 8.3 g. of 2-hydrazinobenzothiazole is added followed by 7.4 g. of 4-methylcinnamonitrile. The reaction mixture is refluxed for 4 hours then is cooled. The precipitate formed is collected by filtration and washed with ethanol, then water, to give 13.7 g. of crude product. This material is recrystallized from 2-methoxyethanol, filtered and washed with hexane then methanol to yield 8.55 g. of 2-(3-amino-5-p-tolyl-2-pyrazolin-1-yl)benzothiazole as colorless prisms, m.p. 282°–285° C.

(B) A mixture of 3.5 g. of the preceding product, 150 mg. of 4-dimethylaminopyridine and 25 ml. of propionic anhydride is refluxed for 2 hours. The reaction mixture is then poured into water and this mixture is allowed to stand at room temperature for 16 hours. The separated solid is collected by filtration. The solid is dissolved in dichloromethane. The organic solution is passed through a short column of a hydrous magnesium silicate. The effluent is concentrated while adding hexane until turbidity results. The solution is cooled, then filtered to collect a solid. The solid is again dissolved in dichloromethane, columnized and recrystallized as described above to give 2.45 g. of the desired product as colorless prisms, m.p. 208°–209° C.

EXAMPLE 2

N-[1-(2-Benzothiazolyl)-5-phenyl-2-pyrazolin-3-yl]acetamide

A 460 mg. amount of sodium metal is dissolved in 150 ml. of absolute ethanol, then 16.5 g. of 2-hydrazinobenzothiazole is added, followed by 12.9 g. of cinnamonitrile. The reaction mixture is refluxed for 16 hours, then is cooled. Some of the solvent is removed in vacuo and the mixture is filtered. The precipitate is washed with hexane to give 25.67 g. of 2-(3-amino-5-phenyl-2-pyrazolin-1-yl)benzothiazole as tan crystals.

A mixture of 3.95 g. of the preceding product, 200 mg. of 4-dimethylaminopyridine and 25 ml. of acetic anhydride is refluxed for 2 hours. Then the solution is cooled and the solvent is evaporated in vacuo to give a solid. The solid is recrystallized from acetone/hexane. The recrystallized product is dissolved in dichloromethane. This solution is columnized and recrystallized as described in Example 1(B) to yield 1.95 g. of the product of the Example as pale yellow prisms, m.p. 220°–222° C.

EXAMPLE 3

| Preparation of Compressed Tablet | |
|---|---|
| Ingredient | mg./tablet |
| Active Compound | 0.5–500 |
| Dibasic Calcium Phosphate N.F. | qs |
| Starch USP | 40 |
| Modified Starch | 10 |
| Magnesium Stearate USP | 0.1–5.0 (% w/w) |

EXAMPLE 4

| Preparation of Compressed Tablet | |
|---|---|
| Ingredient | mg./tablet |
| Active Compound | 0.5–500 |
| Dibasic Calcium Phosphate N.F. | qs |
| Starch USP | 40 |
| Modified Starch | 10 |
| *Surfactant, e.g. | |
| Sodium Lauryl Sulfate | 0.1–2.0 (% w/w) |
| Magnesium Stearate USP | 0.1–5.0 (% w/w) |

*Other surface active agents such as disodium sulfosuccinate and nonionic surface active agents such as Span ® Tween ® may also be employed.

EXAMPLE 5

| Preparation of Compressed Tablet | |
|---|---|
| Ingredient | mg./tablet |
| Active Compound | 0.5–500 |
| Direct Compression Sugar Agent e.g. Emdex | qs |
| Magnesium Stearate | 0.1–3.0 (% w/w) |

EXAMPLE 6

| Preparation of Hard Shell Capsule | |
|---|---|
| Ingredient | mg./capsule |
| Active Compound | 0.5–500 |
| Lactose, Spray Dried | qs |
| Magnesium Stearate | 0.1–3.0 (% w/w) |

EXAMPLE 7

| Preparation of Oral Liquid (Syrup) | |
|---|---|
| Ingredient | % w/v |
| Active Compound | 0.05–5 |
| Liquid Sugar | 75.0 |
| Methyl Paraben USP | 0.18 |
| Propyl Paraben USP | 0.02 |
| Suspending Agent e.g. Avicel | 0.5–1.0 |
| Flavoring Agent | qs |
| Purified Water qs ad | 100.0 |

EXAMPLE 8

Preparation of Oral Liquid (Elixir)

| Ingredient | % w/v |
|---|---|
| Active Compound | 0.05–5 |
| Alcohol USP | 12.5 |
| Glycerine USP | 45.0 |
| Syrup USP | 20.0 |
| Flavoring Agent | qs |
| Purified Water qs ad | 100.0 |

EXAMPLE 9

Preparation of Oral Suspension (Syrup)

| Ingredient | % w/v |
|---|---|
| Active Compound | 0.05–5 |
| Polysorbate 80 USP | 0.1 |
| Magnesium Aluminum Silicate, Colloidal | 0.3 |
| Dye | 0.001–0.5 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 10

Preparation of Injectable Solution

| Ingredient | % w/v |
|---|---|
| Active Compound | 0.05–5 |
| Benzyl Alcohol N.F. | 0.9 |
| Water for Injection | 100.0 |

EXAMPLE 11

Preparation of Injectable Oil

| Ingredient | % w/v |
|---|---|
| Active Compound | 0.05–5 |
| Benzyl Alcohol | 1.5 |
| Sesame Oil qs ad | 100.0 |

EXAMPLE 12

Preparation of Intra-articular Product

| Ingredient | Amount |
|---|---|
| Active Compound | 2–20 mg. |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 13

Preparation of Injectable Depo Suspension

| Ingredient | % w/v |
|---|---|
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs |
| Water for Injection qs ad | 100.0 |

EXAMPLE 14

Preparation of Topical Cream

| Ingredient | % w/w |
|---|---|
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 15

Preparation of Topical Ointment

| Ingredient | % w/w |
|---|---|
| Active Compound | 0.05–5 |
| Cholesterol | 3 |
| Stearyl Alcohol | 3 |
| White Wax | 8 |
| Petrolatum, White USP qs | 100 |

We claim:

1. A compound selected from the group consisting of those of the formula:

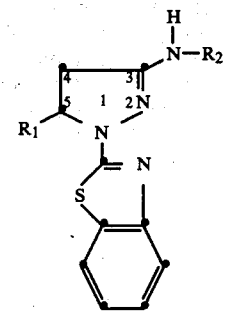

wherein $R_1$ is phenyl or p-tolyl; $R_2$ is $CO-R_3$ where $R_3$ is lower alkyl ($C_1$–$C_4$) and the pharmacologically acceptable acid-addition salts thereof.

2. The compound according to claim 1, N-[1-(2-benzothiazolyl)-5-p-tolyl-2-pyrazolin-3-yl]propionamide.

3. The compound according to claim 1, N-[1-(2-benzothiazolyl)-5-phenyl-2-pyrazolin-3-yl]acetamide.

4. The method of treating bacterial and/or fungal infections in a mammal which comprises administering to said mammal an effective amount of a compound as defined in claim 1, 2 or 3.

* * * * *